(12) United States Patent
Kamen et al.

(10) Patent No.: US 9,375,195 B2
(45) Date of Patent: Jun. 28, 2016

(54) SYSTEM AND METHOD FOR REAL-TIME ULTRASOUND GUIDED PROSTATE NEEDLE BIOPSY BASED ON BIOMECHANICAL MODEL OF THE PROSTATE FROM MAGNETIC RESONANCE IMAGING DATA

(71) Applicants: Ali Kamen, Skillman, NJ (US); Tommaso Mansi, Westfield, NJ (US); Bogdan Georgescu, Plainsboro, NJ (US); Dorin Comaniciu, Princeton Junction, NJ (US)

(72) Inventors: Ali Kamen, Skillman, NJ (US); Tommaso Mansi, Westfield, NJ (US); Bogdan Georgescu, Plainsboro, NJ (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 534 days.

(21) Appl. No.: 13/905,939

(22) Filed: May 30, 2013

(65) Prior Publication Data

US 2013/0324841 A1  Dec. 5, 2013

Related U.S. Application Data

(60) Provisional application No. 61/653,552, filed on May 31, 2012.

(51) Int. Cl.

| | |
|---|---|
| *G06K 9/00* | (2006.01) |
| *A61B 8/08* | (2006.01) |
| *A61B 8/13* | (2006.01) |
| *A61B 10/02* | (2006.01) |
| *A61B 5/00* | (2006.01) |
| *G06T 7/00* | (2006.01) |
| *A61B 5/05* | (2006.01) |
| *A61B 5/055* | (2006.01) |
| *A61B 8/14* | (2006.01) |
| *A61B 8/00* | (2006.01) |

(52) U.S. Cl.
CPC ........... *A61B 8/0841* (2013.01); *A61B 5/7425* (2013.01); *A61B 8/13* (2013.01); *A61B 8/463* (2013.01); *A61B 8/485* (2013.01); *A61B 8/5261* (2013.01); *A61B 10/0233* (2013.01); *A61B 10/0241* (2013.01); *G06T 7/0028* (2013.01); *A61B 5/055* (2013.01); *A61B 8/14* (2013.01); *A61B 8/4254* (2013.01); *A61B 8/483* (2013.01); *G06T 2207/10136* (2013.01); *G06T 2207/30081* (2013.01)

(58) Field of Classification Search
USPC ......... 382/100, 103, 106–107, 128–133, 154, 382/162, 168, 173, 181, 219, 232, 254, 266, 382/274, 276, 285, 291, 305, 312; 378/4, 378/21; 600/438, 411, 407
See application file for complete search history.

(56) References Cited

U.S. PATENT DOCUMENTS

| | | | |
|---|---|---|---|
| 8,073,252 B2 | 12/2011 | Florin et al. | |
| 2003/0100828 A1* | 5/2003 | Engelhard | A61B 5/055 600/411 |

(Continued)

*Primary Examiner* — Seyed Azarian (57) ABSTRACT

A method and system for real-time ultrasound guided prostate needle biopsy based on a biomechanical model of the prostate from 3D planning image data, such as magnetic resonance imaging (MRI) data, is disclosed. The prostate is segmented in the 3D ultrasound image. A reference patient-specific biomechanical model of the prostate extracted from planning image data is fused to a boundary of the segmented prostate in the 3D ultrasound image, resulting in a fused 3D biomechanical prostate model. In response to movement of an ultrasound probe to a new location, a current 2D ultrasound image is received. The fused 3D biomechanical prostate model is deformed based on the current 2D ultrasound image to match a current deformation of the prostate due to the movement of the ultrasound probe to the new location.

31 Claims, 6 Drawing Sheets

(56) References Cited

U.S. PATENT DOCUMENTS

| | | | |
|---|---|---|---|
| 2009/0326363 A1* | 12/2009 | Li | A61B 8/12 600/411 |
| 2010/0286517 A1* | 11/2010 | Kamen | A61B 10/0241 600/438 |
| 2011/0116698 A1* | 5/2011 | Weis | G06K 9/6207 382/131 |
| 2013/0034282 A1 | 2/2013 | Kaufman et al. | |
| 2013/0064439 A1* | 3/2013 | Khurd | G06K 6/6226 382/131 |

* cited by examiner

SYSTEM AND METHOD FOR REAL-TIME ULTRASOUND GUIDED PROSTATE NEEDLE BIOPSY BASED ON BIOMECHANICAL MODEL OF THE PROSTATE FROM MAGNETIC RESONANCE IMAGING DATA

This application claims the benefit of U.S. Provisional Application No. 61/653,552, filed May 31, 2012, the disclosure of which is herein incorporated by reference.

BACKGROUND OF THE INVENTION

The present invention relates to ultrasound guided prostate needle biopsies, and more particularly, to ultrasound guided prostate needle biopsies based on a biomechanical model of the prostate from magnetic resonance imaging data.

Prostate cancer is typically diagnosed by using a transrectal ultrasound (US) guided biopsy, which is typically prescribed as a result of an elevated prostate-specific antigen (PSA) level or due to the detection of a palpable nodule during a digital rectal examination (DRE). The introduction of image guided biopsy using US has substantially increased the accuracy of biopsy, as compared with the very poor accuracy of performing blind biopsy, resulting in transrectal US guidance becoming the universally accepted methodology for prostate biopsy. However, while transrectal US guided prostate biopsy is a clinically accepted methodology, the overall procedure results demonstrate a low sensitivity of approximately 60%, with only 25% positive predictive value. Consequently, repeat biopsies are often required for a definitive diagnosis. For example, in more than 20% of cancer studies, there is a requirement of more than one biopsy session to reach a diagnosis decision.

Magnetic resonance (MR) imaging can clearly depict not only the prostate gland, but also its substructure including the central, transitional, and peripheral zones. T2-weighted MR images can visualize nodules in the peripheral zone of the prostate. Localizing the tumor foci and the peripheral zone with MR imaging prior to the prostate biopsy may increase the overall cancer detection rate. Localizing the tumor foci and the peripheral zone with MR imaging before the prostate biopsy may increase the overall cancer detection rate. In addition, functional information can be acquired with techniques like diffusion weighted imaging (DWI), dynamic contrast imaging (DCE), and chemical shift imaging (CSI) to further characterize the prostatic tumor tissue. Using this information during US-guided biopsy can improve the sensitivity of the biopsy procedure. For example, in a known technique, endorectal MR imaging findings of suspected tumor foci were used to guide the placement of needles during transrectal US-guided biopsy. By localizing suspected tumor lesions or targets on the endorectal MR image and by visually correlating the locations to US images during transrectal US-guided biopsy, the accuracy of the transrectal US-guided biopsy, aided by using MR imaging, was 67% in a study of 33 patients. The data for this study underwent a tedious visual inspection, which cannot be implemented as a clinical routine.

There exists a need to enhance the sensitivity in detecting malignant lesions during a prostate biopsy procedure.

BRIEF SUMMARY OF THE INVENTION

The present invention provides a method and system for an ultrasound (US) guided prostate needle biopsy using a biomechanical model of the prostate from magnetic resonance (MR) imaging data. Embodiments of the present invention use MR imaging to localize tumors and the peripheral zone of the prostate and use this information during the ultrasound guided prostate biopsy to align the place the needle into focal lesions. Embodiments of the present invention provide an automated process, which is important for clinical implementation. Embodiments of the present invention map the lesions localized in the MR image data onto the US acquisition during a biopsy scan and also provide real-time updates of the derived locations of the lesions due to changes in the US scanning plane and subsequent deformations of the prostate caused by the US probe.

In one embodiment of the present invention, a prostate is segmented in a 3D ultrasound image of a patient. A reference patient-specific biomechanical model of the prostate extracted from a 3D planning image of the patient is fused to a boundary of the segmented prostate in the 3D ultrasound image, resulting in a fused 3D biomechanical prostate model. In response to movement of an ultrasound probe to a new location, a current 2D ultrasound image acquired by the ultrasound probe at the new location is received. The fused 3D biomechanical prostate model is deformed based on the current 2D ultrasound image to match a current deformation of the prostate due to the movement of the ultrasound probe to the new location.

These and other advantages of the invention will be apparent to those of ordinary skill in the art by reference to the following detailed description and the accompanying drawings.

DETAILED DESCRIPTION

The present invention relates to a method and system for ultrasound (US) guided prostate needle biopsy based on a biomechanical model of the prostate from magnetic resonance (MR) imaging data. Embodiments of the present invention are described herein to give a visual understanding of the US guided prostate biopsy method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide increased sensitivity to prostate biopsy procedures to detect prostate cancer. Typically, a prostate biopsy id performed systematically under US imaging guidance, which may lack sensitivity in detecting malignant lesions. In order to enhance the sensitivity of the prostate biopsy, it is possible to use suspected lesion localization information from a high quality 3D scan, such as an MR volume, during the prostate biopsy procedure. This lesion localization information helps in the optimal placement of the needle cores in order to take sufficient and accurate pathological samples, and thus increase the detection sensitivity. Embodiments of the present invention fuse an MR image data of a patient with real-time US images acquired during a biopsy scan to provide improved targeting of suspecting tumor or lesions in the prostate. In addition, embodiments of the present invention predict a deformation of the prostate happening in real-time as a result of changing US probe location and orientation and use the predicted deformation of the prostate to update the MR based lesion localization information mapped onto the real-time ultrasound plane and enhance the real-time targeting accuracy.

Figure 1:
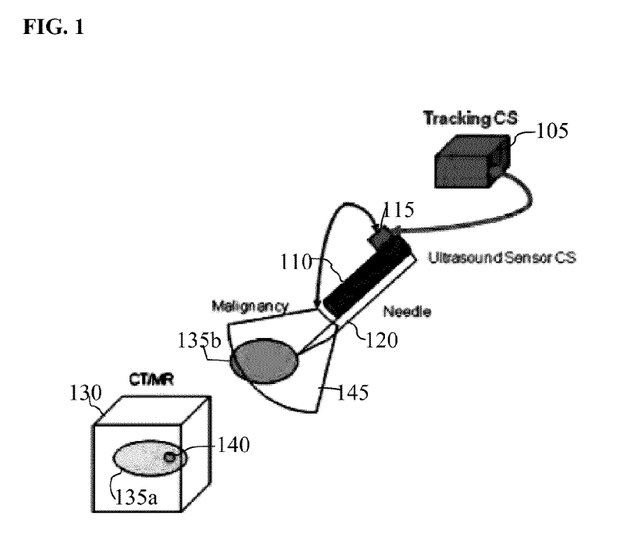
FIG. 1 illustrates a system for implementing real-time ultrasound guiding prostate needle biopsies according to an embodiment of the present invention.

FIG. 1 illustrates a system for implementing real-time ultrasound guiding prostate needle biopsies according to an embodiment of the present invention. The system includes an external tracking system 105 that tracks an ultrasound (US) probe 110 in a stationary coordinate system, i.e., a so-called fixed coordinate system. The probe 110, which may be an US transducer, is tracked by placement of a tracking sensor 115 on the probe 110. The tracking sensor 115 may be a magnetic tracking sensor, but the present invention is not limited thereto. A needle 120, which is used for biopsy purposes, is attached to the probe 110. The system further includes a computer (not shown but described later in FIG. 9) that can cause a reference image 130 of a prostate 135a that includes a lesion 140 to be displayed. For example, the reference image 130 may be an MR image or a computed tomography (CT) image.

A set of two-dimensional (2D) ultrasound images can be acquired using a free-hand 3D sweep 45 covering the prostate 35b. The tracking information of the US probe 110 along with calibration information of the US probe 110 enables generation of pseudo three-dimensional (3D) data sets that consist of the arbitrarily (due to freehand acquisition) oriented 2D US images in 3D. On the other hand, reference image 130 (e.g., MR or CT image) is specified in the coordinate system of the scanning device used to acquire the reference image 130. An image based registration technique, according to an exemplary embodiment of the present invention, establishes a transformation that is required to map the reference image 130 onto the US images in 3D. The specifics of this registration and the dependent components required for this registration process are discussed in greater detail below.

Figure 2:
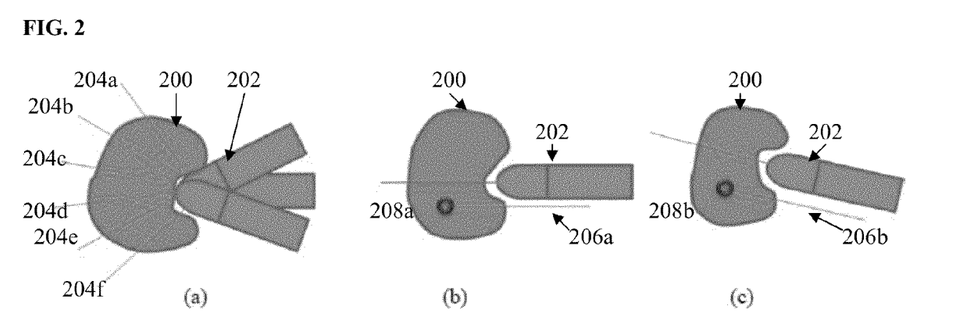
FIG. 2 illustrates movement of an ultrasound probe to acquire a free-hand 3D sweep of the prostate and to align a needle with a target position in the prostate.

FIG. 2 illustrates movement of an US probe to acquire a free-hand 3D sweep of the prostate and to align a needle with a target position in the prostate. Image (a) of FIG. 2 illustrates a free-hand 3D sweep of the prostate 200 using the US probe 202. As shown in image (a) of FIG. 2, the US probe 202 is moved to various positions with respect to the prostate 200 and a 2D US image is acquired along a 2D imaging plane 204a-204f of the US probe 202 at each position. The 2D images acquired during the 3D sweep of the prostate 200 can then be reconstructed into a 3D US image using tracking information of the US probe 202 along with calibration information of the US probe 202.

Images (b) and (c) of FIG. 2 show movement of the US probe 202 to align a trajectory 206a and 206b of a needle guide attached to the US probe with a lesion position 208a and 208b that is overlaid based on the information from an MR image. As shown in images (b), the US probe 202 must be moved to align the needle trajectory 206a with the lesion position 208a, and this movement causes a deformation of anatomy of the prostate 200 as compared to the prostate during the free-hand sweep or the planning 3D scan (e.g., from MRI). This deformation makes the MR based anatomical information that was aligned to the prostate in the 3D US image generated from the freehand sweep obsolete. As shown in image (c), the US probe 202 must be moved again to align the needle trajectory 206b with another lesion position 208b, which causes another deformation of the prostate 200 by the US probe 202.

Figure 3:
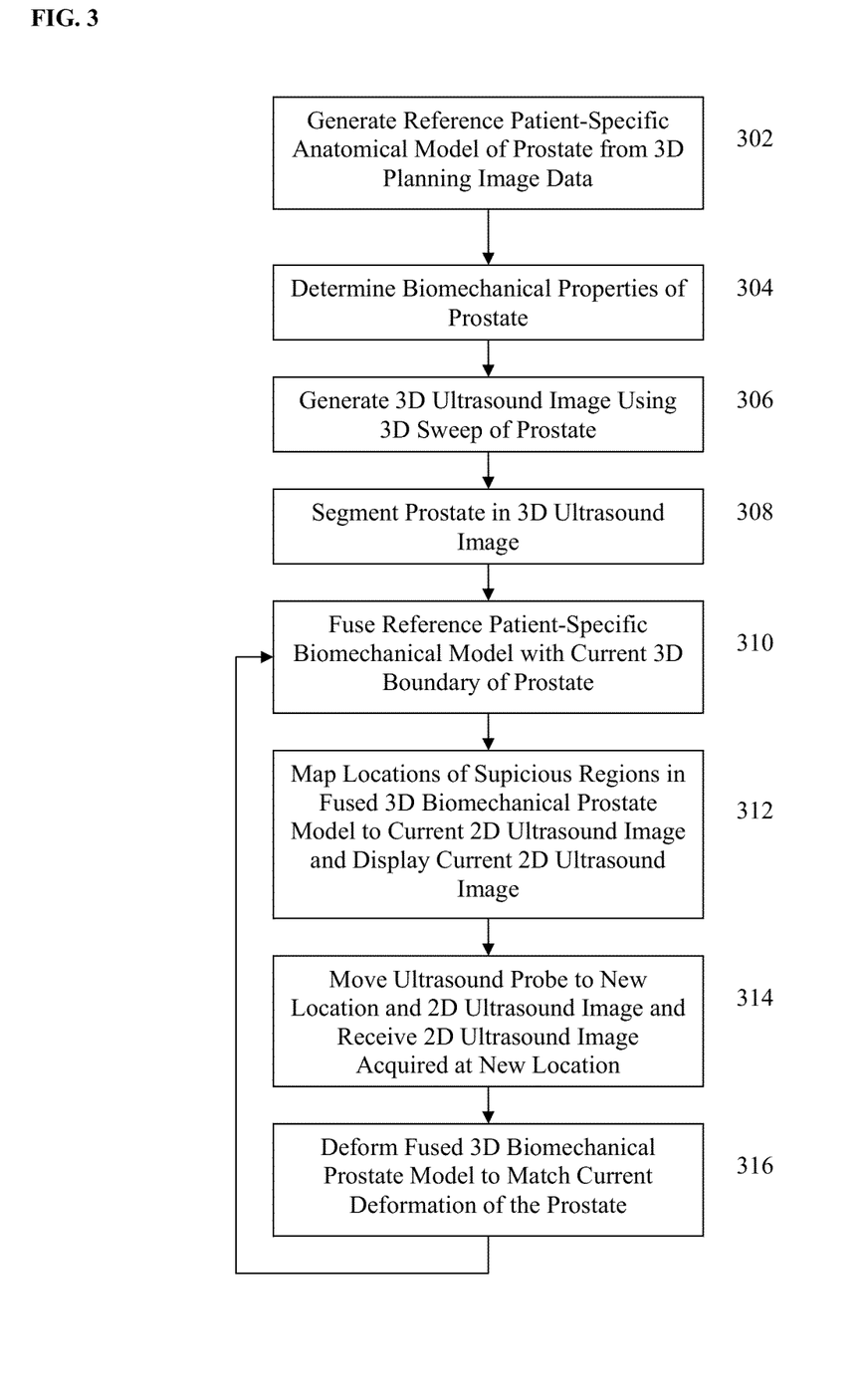
FIG. 3 illustrates a method for ultrasound guided prostate needle biopsy according to an embodiment of the present invention.

FIG. 3 illustrates a method for US guided prostate needle biopsy according to an embodiment of the present invention. The method of FIG. 3 fuses a patient-specific model of the prostate generated from 3D planning image data, such as MR data, with real-time ultrasound images to target suspicious regions in the prostate, and adjusts the fused prostate model to reflect deformations of the prostate due to the ultrasound probe based on ultrasound probe tracking data and the biomechanical properties of the prostate.

Figure 4:
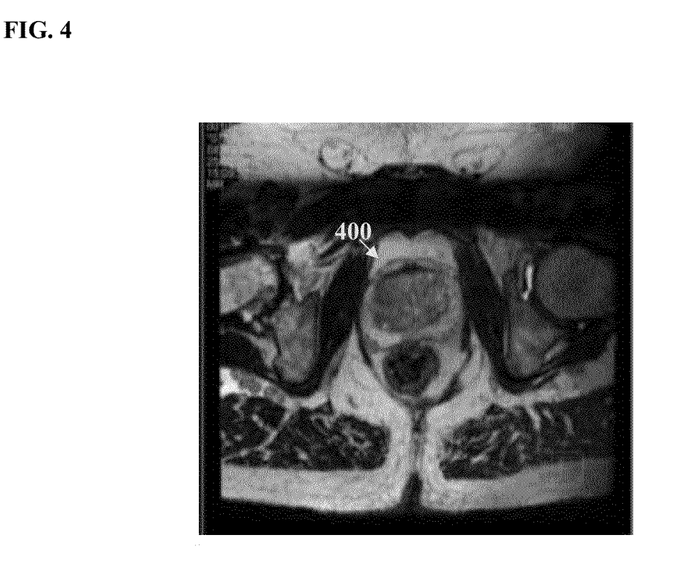
FIG. 4 illustrates prostate segmentation in an exemplary magnetic resonance image.

Referring to FIG. 3, at step 302, a reference patient-specific anatomical model of the prostate is generated from 3D planning image data of the patient. In a possible implementation, step 302 may occur in a planning phase prior to the biopsy procedure. In particular, in a planning phase prior to the biopsy procedure, 3D planning image data of the patient is acquired using an image acquisition device. In an advantageous embodiment, the 3D planning image data may be a 3D MR image data of the patient acquired using an MR scanner, but the present invention is not limited thereto and other imaging modalities, such as CT may be used to generate the 3D planning image data. Once the 3D planning image data of the patient is acquired, the prostate is segmented in the 3D planning image data. The prostate may be segmented in the 3D planning image data manually or by using a semi-automatic or a fully automatic prostate segmentation technique. For example, semi-automatic prostate segmentation may be performed using graph cuts segmentation based on foreground (prostate) and background seeds input by a user. Other semi-automatic techniques, such as shape-constrained segmentation based on level-sets or machine learning based approaches may be used as well. For example, the prostate may be segmented using fully automatic marginal space learning (MSL)-based prostate segmentation technique, as described in United States Published Patent Application No. 2011/00116698, which is incorporated herein by reference patient-specific anatomical model of the prostate. FIG. 4 illustrates prostate segmentation in an exemplary MR image. As shown in FIG. 4, the border of the prostate 400 is segmented in the MR image.

In addition to segmenting the prostate, suspicious regions of the prostate are also identified in the 3D planning image data and the locations of the suspicious regions are included in the reference. The suspicious regions can be identified manually by a clinician or automatically using image-based detection techniques. For example, nodules in the peripheral zone of the prostate can be visualized using T2-weighted MR images. The locations of the tumor foci and the peripheral zone in MR image data can be identified and included in the reference patient-specific anatomical model of the prostate. In addition, functional information can be acquired with techniques like diffusion weighted imaging (DWI), dynamic contrast imaging (DCE), chemical shift imaging (CSI), and MRI spectroscopy to further characterize the prostatic tumor tissue.

Returning to FIG. 3, at step 304, biomechanical properties of the prostate are determined. In an advantageous implementation, the biomechanical properties include values for the Young's modulus and the Poisson's ratio for the prostate. As is well known, the Young's modulus for the prostate is a measure of stiffness of the prostate tissue and the Poisson's ratio for the prostate is the negative ratio of transverse to axial strain for the prostate tissue. In one possible implementation, nominal values for the biomechanical properties reported from literature can be used for the biomechanical properties of the patient's prostate. In another possible implementation, elastography scans of the patient's prostate tissue can be acquired and personalized values for the biomechanical properties of the patient's prostate can be extracted from elastography scans of the patient. In a possible embodiment, step 304 can also be performed in a planning phase prior to the biopsy procedure. The reference patient-specific anatomical model of the prostate and the biomechanical properties of the patient's prostate result in a reference patient-specific biomechanical model of the prostate.

At step 306, at the beginning of the guided biopsy session, a 3D sweep of tracked ultrasound images is acquired using an ultrasound probe and ultrasound probe tracking system. A 3D ultrasound image is generated from 3D sweep. In particular, the ultrasound probe is tracking by the tracking system and the 3D ultrasound image is reconstructed from the 2D ultrasound images acquired during the sweep based on the tracking information of the ultrasound probe along with calibration information of the ultrasound probe. The tracking system may use a magnetic tracking sensor to track the ultrasound probe, as shown in FIG. 1. Alternatively, it is also possible that mechanical or optical tracking can be used instead of magnetic tracking to track the position and orientation of the ultrasound probe.

Figure 5:
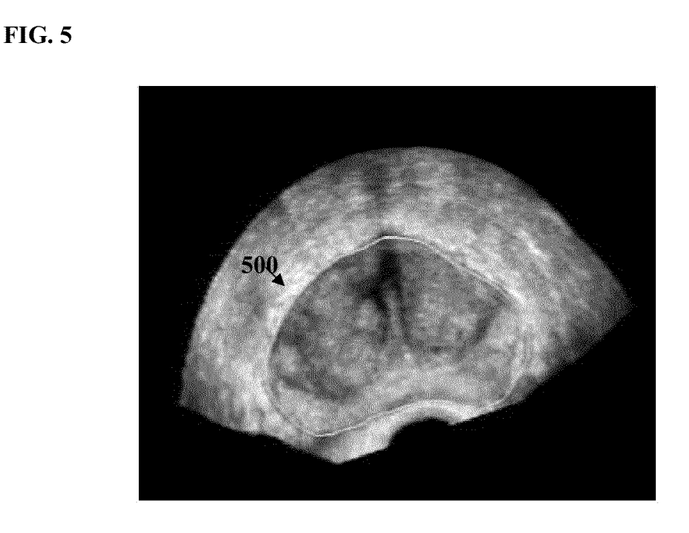
FIG. 5 illustrates exemplary prostate segmentation in a 3D ultrasound image.

At step 308, a current 3D boundary of the prostate is detected by automatically segmenting the prostate in the 3D ultrasound image. The prostate segmentation in the 3D ultrasound image gives a current deformation state of the prostate. In a possible implementation, the prostate can be segmented in the 3D ultrasound image using a graph cuts segmentation based on foreground and background seeds automatically determined from the patient-specific anatomical model of the prostate generated from the 3D planning image data. In this case, a binary mask representing the boundary of prostate segmented in the 3D planning image data is mapped to the 3D US image using an initial rigid registration between the 3D planning image and the 3D US image. Foreground seeds are generated by shrinking the binary mask, for example by 20%, and selecting points inside the shrunken binary mask. Background seeds are generated by expanding the binary mask, for example by 20%, and selecting points outside of the binary mask. Graph cuts or Multi-label random walker segmentation can then be used to segment the prostate based on the automatically determined seed points. In other possible implementations, other segmentation techniques, such as shape model constrained segmentation based on level-sets or machine learning based approaches (e.g. probabilistic boosting tree with marginal space learning and a statistical shape model), can be used to segment the prostate in the 3D US image. FIG. 5 illustrates exemplary prostate segmentation in a 3D US image. As shown, in FIG. 5 a prostate boundary 500 is segmented in a 3D US image.

Returning to FIG. 3, at step 310, the reference patient-specific biomechanical model is fused with the current 3D boundary of the prostate in order to map the reference patient-specific biomechanical model to the current deformation state of the prostate, resulting in a fused 3D biomechanical prostate model. Immediately after step 308 is performed, the current 3D boundary of the prostate corresponds to the segmentation of the prostate in the 3D ultrasound image. Accordingly, the reference patient-specific biomechanical model from the 3D planning image data (e.g., MR image data) is fused with the segmented 3D prostate model from the 3D ultrasound image. When the method returns to step 310 after step 318, the current 3D boundary of the prostate in the ultrasound is a result deforming the previous fused 3D biomechanical prostate model at step 318.

The reference patient-specific biomechanical model (i.e., the reference patient-specific anatomical model and the biomechanical properties) is fused to the current 3D boundary of the prostate by registering mesh surfaces of the reference patient-specific anatomical model and current 3D boundary based on differences between the boundary of the reference patient-specific anatomical model and the current 3D boundary of the prostate and the biomechanical properties of the prostate using rigid and deformable registrations. For example, biomechanical finite element based registration can also be used to register the extracted boundary of the prostate in the 3D planning data (i.e., the reference patient-specific anatomical model) to the current 3D boundary of the prostate using physically plausible deformations based on the biomechanical properties. The reference patient-specific anatomical model including the suspicious regions (e.g. lesions) from the 3D planning image data is then transformed onto the 3D US image or a real-time 2D US image using the determined deformation field. Such a method for fusing a reference patient-specific anatomical model of the prostate and a current prostate segmentation in a 3D US image is described in greater detail in United States Published Patent Application No. 2010/0286517, which is incorporated herein by reference.

At step 312, locations of suspicious regions from the fused 3D biomechanical prostate model are mapped onto a current 2D US image and displayed, for example by a display device of a computer system. During the biopsy procedure 2D US images are acquired by the US probe in real-time and locations of the suspicious regions are mapped onto the 2D US images to show target locations for the biopsy. The display of the 2D US images including the target locations can be used to guide a clinician performing the biopsy procedure. For example, the locations of suspicious regions (e.g., lesions or tumors) can be displayed as cross-hairs overlaid onto current 2D ultrasound image or as contours overlaid onto current 2D ultrasound image showing boundaries of the suspicious regions using different line-styles or colors. Other information from the 3D planning image data included in the fused 3D biomechanical prostate model may also be displayed as well. In addition to the 2D US image, the fused 3D biomechanical may be displayed as well. In one embodiment, a segmented 2D boundary of the prostate in the current 2D ultrasound image is displayed as an overlaid contour on the current 2D ultrasound image using one line style or color and a cross section of the fused 3D biomechanical prostate model in the imaging plane of the current 2D ultrasound image is displayed as an overlaid contour on the current 2D ultrasound image using a different line style or color.

At step 314, the US probe is moved to a new location and a 2D ultrasound image acquired at the new location is received. In order to perform the biopsy procedure, the clinician moves the ultrasound probe to align the needle attached to the probe with a target location in the prostate. The tracking system tracks the position and orientation of the US probe. 2D ultrasound images are acquired by the US probe in real time during the biopsy procedure. When the US probe is moved to a new position, a 2D ultrasound image acquired by the probe at the new position is received. As described above and illustrated in images (a) and (b) of FIG. 2, the movement of the ultrasound probe causes deformation of the prostate.

At step 316, the fused 3D biomechanical prostate model of the prostate is deformed based on a prostate contour in the current 2D US image, the 3D position and orientation of the US probe, and the biomechanical properties to provide a current 3D boundary of the prostate that matches a current deformation state of the prostate. As the ultrasound probe is moved, the various pieces of information are exploited to estimate the deformation of the prostate resulting from the movement of the ultrasound probe. The fused 3D biomechanical prostate model includes anatomical information from the 3D planning image data and biomechanical properties of the prostate. In addition to the patient-specific anatomical model of the prostate and cavity model including anatomy surrounding the prostate structure may also be detected in the 3D planning image data and included with the fused 3D biomechanical prostate model. More elaborate delineation of prostate surrounding structures and subdivision into substructures such as the bladder, rectum, and muscle can enhance the modeling capability and thus improve the accuracy of the estimated deformation. The 3D position and orientation of the ultrasound probe is known from the tracking system. Based on an extracted contour of the prostate in the real-time 2D ultrasound image, the objective is to deform the fused 3D biomechanical model of the prostate so that the 2D contour as captured through the real-time ultrasound image acquisition matches 2D contours of the prostate reconstructed from the fused 3D biomechanical prostate model.

Figure 6:
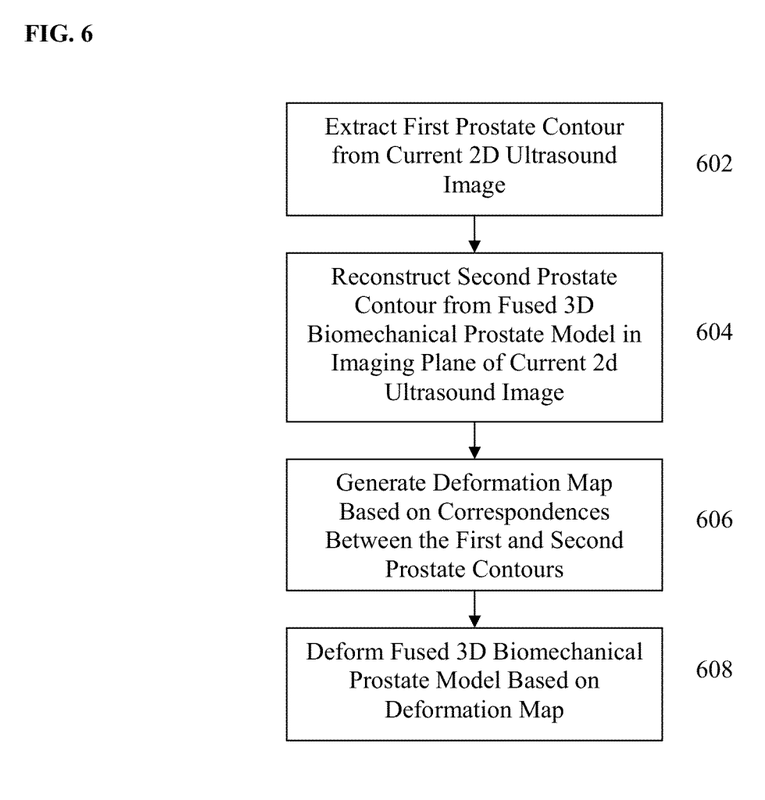
FIG. 6 illustrates a method for deforming a fused 3D biomechanical of the prostate to match a current deformation of the prostate according to an embodiment of the present invention.

FIG. 6 illustrates a method for deforming the fused 3D biomechanical of the prostate to match a current deformation of the prostate according to an embodiment of the present invention. The method of FIG. 6 can be used to implement step 316 of FIG. 3. The method of FIG. 6 results in a deformed 3D biomechanical prostate model that provides the current 3D boundary of the prostate.

Referring to FIG. 6, at step 602, a first 2D prostate contour is extracted from the current 2D US image. In a possible implementation, the first 2D prostate contour can be extracted using graph cuts segmentation or multi-label random walker segmentation based on foreground and background labels. The foreground and background labels can be generated automatically in the current 2D ultrasound image by shrinking and expanding a binary mask representing the 2D boundary of the fused 3D biomechanical prostate model in the current 2D imaging plane, similar to the technique described above in connection with step 308. In addition to graph cuts segmentation or multi-label random walker segmentation, alternative segmentation methods such as Probabilistic boosting tree with marginal space learning and a statistical shape model or a level set segmentation approach with statistical shape models can be used for prostate segmentation the current 2D ultrasound image.

Figure 7:
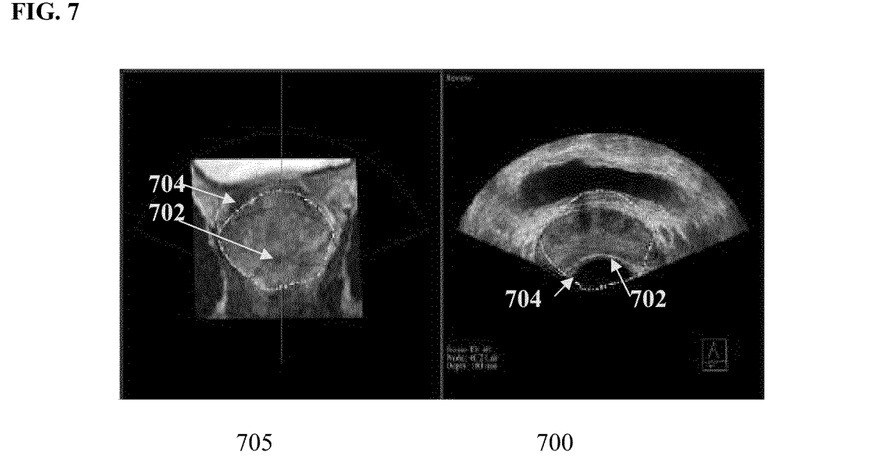
FIG. 7 illustrates exemplary 2D prostate contours extracted from a 2D US image and reconstructed from a 3D prostate model

At step 604, a second 2D prostate contour is reconstructed from the fused 3D biomechanical prostate model in the imaging plane of the current 2D US image. In particular, the current 2D imaging plane of the US probe is determined based on the current 3D position and orientation of the US probe and ultrasound calibration parameters associated with the US probe. The second 2D prostate contour is generated as a cross-section of the fused 3D biomechanical along the current 2D image plane of the US probe. FIG. 7 illustrates exemplary 2D prostate contours extracted from a 2D US image and reconstructed from a 3D prostate model. As shown in FIG. 7, contour 702 is a first prostate contour extracted from a 2D US image 700 and contour 704 is a second prostate contour reconstructed as a cross-section of a fused 3D biomechanical prostate model 705.

Returning to FIG. 6, at step 606, a deformation map is generated based on correspondences between the first 2D prostate contour extracted from the current 2D US image and the second 2D prostate contour reconstructed from the fused 3D biomechanical prostate model. Corresponding points on the first and second 2D prostate contours can be determined using an Iterative Closest Point (ICP) algorithm. Iterative Closest Point (ICP) is a well-known algorithm for rigid point set registration. ICP iteratively assigns correspondences based on a closest distance criterion and finds the least-squares rigid transformation relating the two point sets. The algorithm then re-determines the correspondences and is iterated until a local minimum is reached. Once the corresponding points on the first and second 2D prostate contours are determined, a deformation map is generated that maps each point on the second 2D prostate contour to the corresponding point on the first 2D prostate contour. This deformation map provides the deformation of the prostate within the 2D imaging plane of the current 2D US image.

Figure 8:
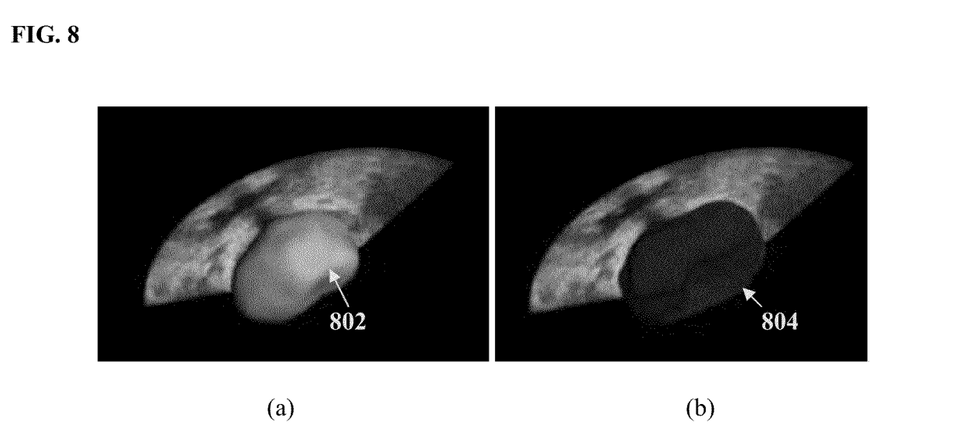
FIG. 8 illustrates exemplary deformation of a fused 3D biomechanical prostate model to match a current boundary of the prostate.

At step 608, the fused 3D biomechanical prostate model is deformed based on deformation map. In particular, the deformation map is prescribed onto the 3D biomechanical prostate model and the fused 3D biomechanical prostate model is deformed according to the deformation map. The prescribed deformation is then propagated outside of the current imaging plane over the 3D boundary of the fused 3D biomechanical model based on the biomechanical properties of the biomechanical model. This results in the deformation map being propagated into a 3D deformation field which is applied to the boundary of the 3D biomechanical prostate model to deform the entire 3D biomechanical prostate model to estimate the current 3D boundary of the prostate. FIG. 8 illustrates exemplary deformation of a fused 3D biomechanical prostate model to match a current boundary of the prostate. As shown in FIG. 8, image (a) shows a fused 3D biomechanical prostate model 802 and image (b) shows a deformed 3D biomechanical prostate model 804 resulting from deforming the 3D biomechanical prostate model 802 to match a current deformation state of the prostate due to insertion of a trans-rectal ultrasound probe.

Returning to FIG. 3, once the fused 3D biomechanical prostate model is deformed to match the current 3D boundary of the prostate at step 316, the method returns to step 310 and the reference patient-specific biomechanical model extracted generated from the 3D planning image data is fused to the current 3D boundary of the prostate provided by the deformed fused 3D biomechanical prostate model, resulting in a new fused 3D biomechanical prostate model. The method then proceeds to step 312, at which the suspicious regions from the new fused 3D biomechanical prostate model are mapped to the current 2D US image and the 2D US image showing the target suspicious regions is displayed. Steps 314, 316, 310, and 312 can be performed in real-time for each 2D US image as each 2D US image is acquired in a biopsy procedure. Accordingly, as each 2D US image is received in the biopsy procedure, the current 3D boundary of the prostate due to the movement of the US probe is determined, the reference patient-specific biomechanical model generated from the 3D planning image data is fused to the current 3D boundary of the prostate, and the each 2D US image is displayed in real time with mapped target locations and possibly other information from the reference patient-specific biomechanical model.

Variations and extensions of the above described embodiments of the present invention are disclosed as follows.

3D wobblers or 2D matrix arrays may be used to generate a native 3D ultrasound volume as opposed to a compounded 3D ultrasound volume generated from a set of tracked 2D ultrasound images.

A multi-slice 2D MR acquisition may be used as the planning image data as opposed to a single 3D MR planning dataset.

A statistical shape model may be used to model the prostate deformation as opposed to the biomechanical model described above.

As an alternative to propagating the deformation map over the 3D boundary of the fused 3D biomechanical prostate model, as described at step 608 of FIG. 6, a set of forces can be derived on the surface of the ultrasound probe acting upon the prostate model and deforming the prostate boundary with the specific constraint that the ultrasound plane contour matches the contour resulting from the intersection of the ultrasound plane with the deformed 3D biomechanical prostate model.

In another possible implementation, step 608 of FIG. 6 can be extended to take into account surrounding structures that are tethered to some fixed point in space, not letting the prostate move. In this case, the following equation specifies forces acting on the prostate:

$$M^P \frac{\partial^2 U^P}{\partial t^2} + C^P \frac{\partial U^P}{\partial t} + K^P U^P = F^P + F^S,$$

where $U^P$ s the prostate deformation, $M^P$ is the mass of the prostate, $C^P$ s the damping factor of the prostate, $K^P$ is the stiffness of the prostate, $F^P$ is the external force from the ultrasound probe, and $F^S$ is the force from the surrounding stiffness. This equation can be solved for $U^P$ using co-rotational finite elements to cope with large deformations and rotations.

Figure 9:
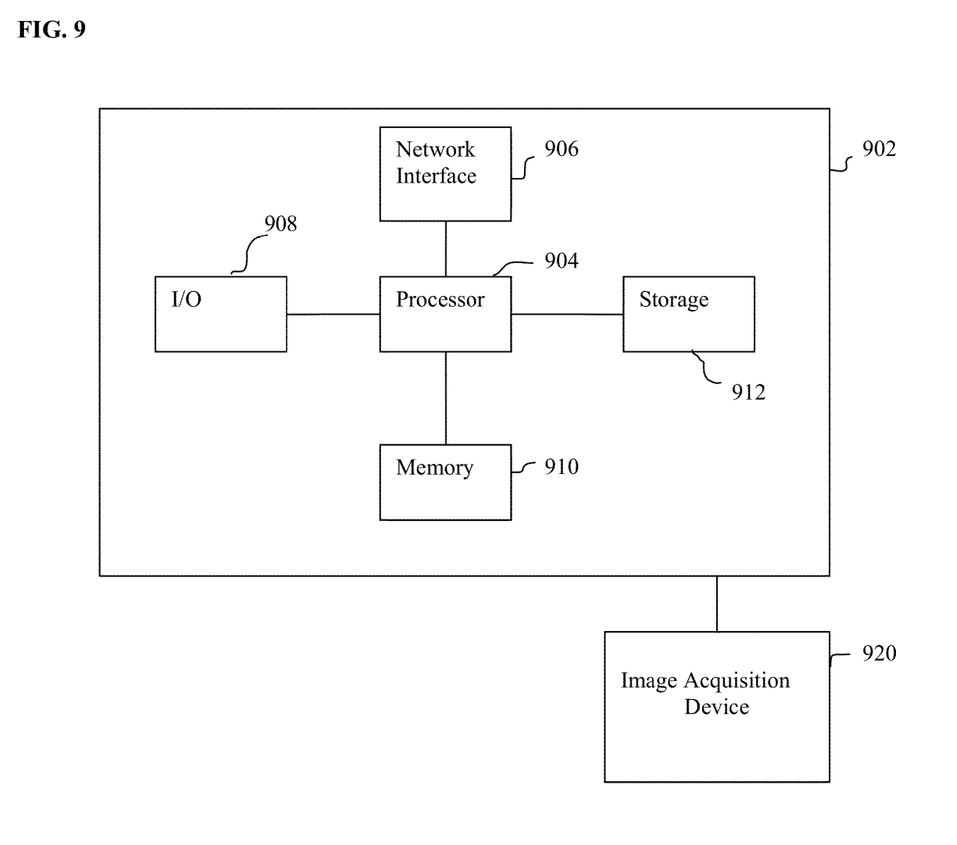
FIG. 9 is a high-level block diagram of a computer capable of implementing the present invention.

The above-described methods for ultrasound guided prostate needle biopsy based on a biomechanical model of the prostate from 3D planning image data using may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 3 and 6 may be defined by the computer program instructions stored in the memory 910 and/or storage 912 and controlled by the processor 904 executing the computer program instructions. An image acquisition device 920, such as an MR scanning device, can be connected to the computer 902 to input image data to the computer 902. It is possible to implement the image acquisition device 920 and the computer 902 as one device. It is also possible that the image acquisition device 920 and the computer 902 communicate wirelessly through a network. The computer 902 also includes one or more network interfaces 906 for communicating with other devices via a network. The computer may communicate with a tracking system, such as the tracking system illustrated in FIG. 1 via the network interface 906 or via a direct wired or wireless connection. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising, comprising:
segmenting a prostate in a 3D ultrasound image of a patient by mapping a binary mask of the reference patient-specific biomechanical model of the prostate to the 2D ultrasound image;
fusing a reference patient-specific biomechanical model of the prostate extracted from a 3D planning image of the patient to a boundary of the segmented prostate in the 3D ultrasound image, resulting in a fused 3D biomechanical prostate model;
in response to movement of an ultrasound probe to a new location, receiving a current 2D ultrasound image acquired by the ultrasound probe at the new location; and
deforming the fused 3D biomechanical prostate model based on a prostate contour in the current 2D ultrasound image to match a current deformation of the prostate due to the movement of the ultrasound probe to the new location.

2. The method of claim 1, further comprising:
fusing the reference patient-specific biomechanical model of the prostate to a boundary of the deformed fused 3D biomechanical prostate model, resulting in a new fused 3D biomechanical prostate model.

3. The method of claim 2, further comprising:
mapping locations of suspicious regions annotated in the new fused 3D biomechanical prostate model to the current 2D ultrasound image; and
displaying the current 2D ultrasound image with the mapped locations of suspicious regions.

4. The method of claim 3, wherein displaying the current 2D ultrasound image with the mapped locations of suspicious regions comprises:
displaying the locations of suspicious regions as one of cross-hairs overlaid onto current 2D ultrasound image or contours overlaid onto current 2D ultrasound image showing boundaries of the suspicious regions using different line-styles or colors.

5. The method of claim 2, further comprising:
displaying a segmented 2D boundary of the prostate in the current 2D ultrasound image as an overlaid contour on the current 2D ultrasound image using a first line style or color; and
displaying a cross section of the new fused 3D biomechanical prostate model in the imaging plane of the current 2D ultrasound image as an overlaid contour on the current 2D ultrasound image using a second line style or color.

6. The method of claim 1, wherein the reference patient-specific biomechanical model of the prostate comprises a patient-specific anatomical model of the prostate extracted from the 3D planning image of the patient and biomechanical properties of the prostate.

7. The method of claim 6, wherein the biomechanical properties of the prostate are patient-specific biomechanical properties extracted from elastography scans of the patient's prostate.

8. The method of claim 6, wherein the current 2D ultrasound image is received in real time during a needle biopsy procedure, and the steps of fusing the reference patient-specific biomechanical model of the prostate to a boundary of the deformed fused 3D biomechanical prostate model, mapping locations of suspicious regions annotated in the new fused 3D biomechanical prostate model to the current 2D ultrasound image, and displaying the current 2D ultrasound image with the mapped locations of suspicious regions are performed in real time in response to receiving the current 2D ultrasound image.

9. The method of claim 1, wherein the 3D planning image is a 3D magnetic resonance image.

10. The method of claim 1, further comprising:
acquiring a plurality of tracked ultrasound images with a 3D sweep of the prostate by the ultrasound probe; and
generating the 3D ultrasound image from the plurality of tracked ultrasound images.

11. The method of claim 1, wherein segmenting a prostate in a 3D ultrasound image of a patient comprises:
shrinking the mapped binary mask by a predetermined percentage;
automatically selecting foreground seeds from within the shrunken binary mask;
expanding the mapped binary mask by a predetermined percentage;
automatically selecting background seeds outside of the expanded binary mask; and
automatically segmenting the prostate in the 3D ultrasound image based on the automatically selected foreground seeds and the automatically selected background seeds.

12. The method of claim 1, wherein fusing a reference patient-specific biomechanical model of the prostate extracted from a 3D planning image of the patient to a boundary of the segmented prostate in the 3D ultrasound image comprises:
registering the reference patient-specific biomechanical model to the boundary of the segmented prostate in the 3D ultrasound based on differences between a boundary of the reference patient-specific biomechanical model and the boundary of the segmented prostate in the 3D ultrasound and biomechanical properties of the reference patient-specific biomechanical model using rigid and deformable registrations.

13. The method of claim 1, wherein deforming the fused 3D biomechanical prostate model based on a prostate contour in the current 2D ultrasound image to match a current deformation of the prostate due to the movement of the ultrasound probe to the new location comprises:
deforming the fused 3D biomechanical prostate model based on the prostate contour extracted from the 2D ultrasound image, a 3D position and orientation of the ultrasound probe, and biomechanical properties of the fused 3D biomechanical prostate model.

14. The method of claim 1, wherein deforming the fused 3D biomechanical prostate model based on a prostate contour in the current 2D ultrasound image to match a current deformation of the prostate due to the movement of the ultrasound probe to the new location comprises:
extracting a first prostate contour from the current 2D ultrasound image;
reconstructing a second prostate contour from the fused 3D biomechanical prostate model in the imaging plane of the current 2D ultrasound image using a tracked 3D position and orientation of the ultrasound probe;
generating a deformation map showing deformations that map points on the second prostate contour to corresponding points on the first prostate contour; and
deforming the fused 3D biomechanical prostate model based on the deformation map.

15. The method of claim 14, wherein deforming the fused 3D biomechanical prostate model based on the deformation map comprises:
prescribing the deformation map onto the fused 3D biomechanical prostate model;
deforming a boundary of the fused 3D biomechanical prostate model in the imaging plane of the current 2D ultrasound image according to the deformation map; and
propagating the deformation of the boundary of the fused 3D biomechanical prostate model outside of the imaging plane of the current 2D ultrasound image using biomechanical properties of the fused 3D biomechanical prostate model.

16. An apparatus, comprising:
a processor; and
a memory storing computer program instructions, which when executed by the processor cause the processor to perform operations comprising:
segmenting a prostate in a 3D ultrasound image of a patient by mapping a binary mask of the reference patient-specific biomechanical model of the prostate to the 2D ultrasound image;
fusing a reference patient-specific biomechanical model of the prostate extracted from a 3D planning image of the patient to a boundary of the segmented prostate in the 3D ultrasound image, resulting in a fused 3D biomechanical prostate model;
receiving a current 2D ultrasound image acquired by the ultrasound probe that has moved to a new location; and
deforming the fused 3D biomechanical prostate model based on a prostate contour in the current 2D ultrasound image to match a current deformation of the prostate due to the movement of the ultrasound probe to the new location.

17. The apparatus of claim 16, wherein the operations further comprise:
fusing the reference patient-specific biomechanical model of the prostate to a boundary of the deformed fused 3D biomechanical prostate model, resulting in a new fused 3D biomechanical prostate model.

18. The apparatus of claim 16, wherein the reference patient-specific biomechanical model of the prostate comprises a patient-specific anatomical model of the prostate extracted from the 3D planning image of the patient and biomechanical properties of the prostate.

19. The apparatus of claim 16, wherein the 3D planning image is a 3D magnetic resonance image.

20. The apparatus of claim 16, wherein deforming the fused 3D biomechanical prostate model based on a prostate contour in the current 2D ultrasound image to match a current deformation of the prostate due to the movement of the ultrasound probe to the new location comprises:
    deforming the fused 3D biomechanical prostate model based on the prostate contour extracted from the 2D ultrasound image, a 3D position and orientation of the ultrasound probe, and biomechanical properties of the fused 3D biomechanical prostate model.

21. The apparatus of claim 16, wherein deforming the fused 3D biomechanical prostate model based on a prostate contour in the current 2D ultrasound image to match a current deformation of the prostate due to the movement of the ultrasound probe to the new location comprises:
    extracting a first prostate contour from the current 2D ultrasound image;
    reconstructing a second prostate contour from the fused 3D biomechanical prostate model in the imaging plane of the current 2D US image using a tracked 3D position and orientation of the ultrasound probe;
    generating a deformation map showing deformations that map points on the second prostate contour to corresponding points on the first prostate contour; and
    deforming the fused 3D biomechanical prostate model based on the deformation map.

22. A non-transitory computer readable medium storing computer program instructions which when executed by a processor cause the processor to perform operations comprising:
    segmenting a prostate in a 3D ultrasound image of a patient by mapping locations of suspicious regions annotated in the new fused 3D biomechanical prostate model to the current 2D ultrasound image;
    fusing a reference patient-specific biomechanical model of the prostate extracted from a 3D planning image of the patient to a boundary of the segmented prostate in the 3D ultrasound image, resulting in a fused 3D biomechanical prostate model;
    in response to movement of an ultrasound probe to a new location, receiving a current 2D ultrasound image acquired by the ultrasound probe at the new location; and
    deforming the fused 3D biomechanical prostate model based on a prostate contour in the current 2D ultrasound image to match a current deformation of the prostate due to the movement of the ultrasound probe to the new location.

23. The non-transitory computer readable medium of claim 22, wherein the operations further comprise:
    fusing the reference patient-specific biomechanical model of the prostate to a boundary of the deformed fused 3D biomechanical prostate model, resulting in a new fused 3D biomechanical prostate model.

24. The non-transitory computer readable medium of claim 23, wherein the operations further comprise:
    displaying the current 2D ultrasound image with the mapped locations of suspicious regions.

25. The non-transitory computer readable medium of claim 22, wherein the reference patient-specific biomechanical model of the prostate comprises a patient-specific anatomical model of the prostate extracted from the 3D planning image of the patient and biomechanical properties of the prostate.

26. The non-transitory computer readable medium of claim 22, wherein the 3D planning image is a 3D magnetic resonance image.

27. The non-transitory computer readable medium of claim 22, wherein the operations further comprise:
    acquiring a plurality of tracked ultrasound images with a 3D sweep of the prostate by the ultrasound probe; and
    generating the 3D ultrasound image from the plurality of tracked ultrasound images.

28. The non-transitory computer readable medium of claim 22, wherein fusing a reference patient-specific biomechanical model of the prostate extracted from a 3D planning image of the patient to a boundary of the segmented prostate in the 3D ultrasound image comprises:
    registering the reference patient-specific biomechanical model to the boundary of the segmented prostate in the 3D ultrasound based on differences between a boundary of the reference patient-specific biomechanical model and the boundary of the segmented prostate in the 3D ultrasound and biomechanical properties of the reference patient-specific biomechanical model using rigid and deformable registrations.

29. The non-transitory computer readable medium of claim 22, wherein deforming the fused 3D biomechanical prostate model based on a prostate contour in the current 2D ultrasound image to match a current deformation of the prostate due to the movement of the ultrasound probe to the new location comprises:
    deforming the fused 3D biomechanical prostate model based on the prostate contour extracted from the 2D ultrasound image, a 3D position and orientation of the ultrasound probe, and biomechanical properties of the fused 3D biomechanical prostate model.

30. The non-transitory computer readable medium of claim 22, wherein deforming the fused 3D biomechanical prostate model based on a prostate contour in the current 2D ultrasound image to match a current deformation of the prostate due to the movement of the ultrasound probe to the new location comprises:
    extracting a first prostate contour from the current 2D ultrasound image;
    reconstructing a second prostate contour from the fused 3D biomechanical prostate model in the imaging plane of the current 2D US image using a tracked 3D position and orientation of the ultrasound probe;
    generating a deformation map showing deformations that map points on the second prostate contour to corresponding points on the first prostate contour; and
    deforming the fused 3D biomechanical prostate model based on the deformation map.

31. The non-transitory computer readable medium of claim 30, wherein deforming the fused 3D biomechanical prostate model based on the deformation map comprises:
    prescribing the deformation map onto the fused 3D biomechanical prostate model;
    deforming a boundary of the fused 3D biomechanical prostate model in the imaging plane of the current 2D ultrasound image according to the deformation map; and
    propagating the deformation of the boundary of the fused 3D biomechanical prostate model outside of the imaging plane of the current 2D ultrasound image using biomechanical properties of the fused 3D biomechanical prostate model.

* * * * *